(12) United States Patent
Allmendinger et al.

(10) Patent No.: US 9,541,535 B2
(45) Date of Patent: Jan. 10, 2017

(54) AGGLOMERATION AND CHARGE LOSS SENSOR WITH SEED STRUCTURE FOR MEASURING PARTICULATE MATTER

(71) Applicant: EmiSense Technologies, LLC, Ladera Ranch, CA (US)

(72) Inventors: Klaus Allmendinger, San Juan Capistrano, CA (US); Joe Fitzpatrick, Glendale, CA (US); Brett Henderson, Salt Lake City, UT (US); Anthoniraj Lourdhusamy, West Jordan, UT (US); Lee Sorensen, West Jordan, UT (US); James Steppan, Park City, UT (US); Gangquiang Wang, Salt Lake City, UT (US)

(73) Assignee: EmiSense Technologies, LLC, Ladera Ranch, CA (US)

( * ) Notice: Subject to any disclaimer, the term of this patent is extended or adjusted under 35 U.S.C. 154(b) by 265 days.

(21) Appl. No.: 14/166,658

(22) Filed: Jan. 28, 2014

(65) Prior Publication Data
US 2014/0144208 A1    May 29, 2014

Related U.S. Application Data

(60) Division of application No. 13/853,890, filed on Mar. 29, 2013, now Pat. No. 8,671,736, which is a
(Continued)

(51) Int. Cl.
*G01N 33/00* (2006.01)
*G01M 15/10* (2006.01)
(Continued)

(52) U.S. Cl.
CPC .......... *G01N 33/0027* (2013.01); *C23C 30/00* (2013.01); *G01M 15/102* (2013.01); *G01N 15/0656* (2013.01)

(58) Field of Classification Search
CPC .......... G01N 15/0656; G01N 33/0027; G01M 15/102; C23C 30/00
See application file for complete search history.

(56) References Cited

U.S. PATENT DOCUMENTS

| 4,916,384 A | 4/1990 | Ishida |
| 7,872,466 B2 * | 1/2011 | Dorfmueller ...... G01N 15/0656 324/515 |

(Continued)

FOREIGN PATENT DOCUMENTS

| DE | 19536705 A1 | 4/1997 |
| WO | 99/26053 | 5/1999 |

OTHER PUBLICATIONS

"European Search Report" Application No. 12789406.1, 9 pages, mailed Oct. 23, 2014.

*Primary Examiner* — Lisa Caputo
*Assistant Examiner* — Punam Roy
(74) *Attorney, Agent, or Firm* — Jeffrey T. Holman

(57) ABSTRACT

A sensor includes an electrode and a seed structure. The electrode is configured to measure current due to movement of particulate matter relative to the electrode. The seed structure is deposited on the electrode. The seed structure includes a plurality of elongated members extending outward from the surface of the electrode. The elongated members are configured to promote charge transfer to particles and/or agglomerates of the particulate matter during operation of the sensor.

16 Claims, 10 Drawing Sheets

Related U.S. Application Data continuation-in-part of application No. 13/315,146, filed on Dec. 8, 2011, now Pat. No. 8,713,991.

(60) Provisional application No. 61/490,528, filed on May 26, 2011.

(51) Int. Cl.
*G01N 15/06* (2006.01)
*C23C 30/00* (2006.01)

(56) References Cited

U.S. PATENT DOCUMENTS

| | | | |
|---|---|---|---|
| 2010/0264025 A1 | 10/2010 | Nair et al. | |
| 2011/0062973 A1 | 3/2011 | Paterson | |
| 2014/0174155 A1* | 6/2014 | Hong | G01N 27/128 73/31.05 |

\* cited by examiner

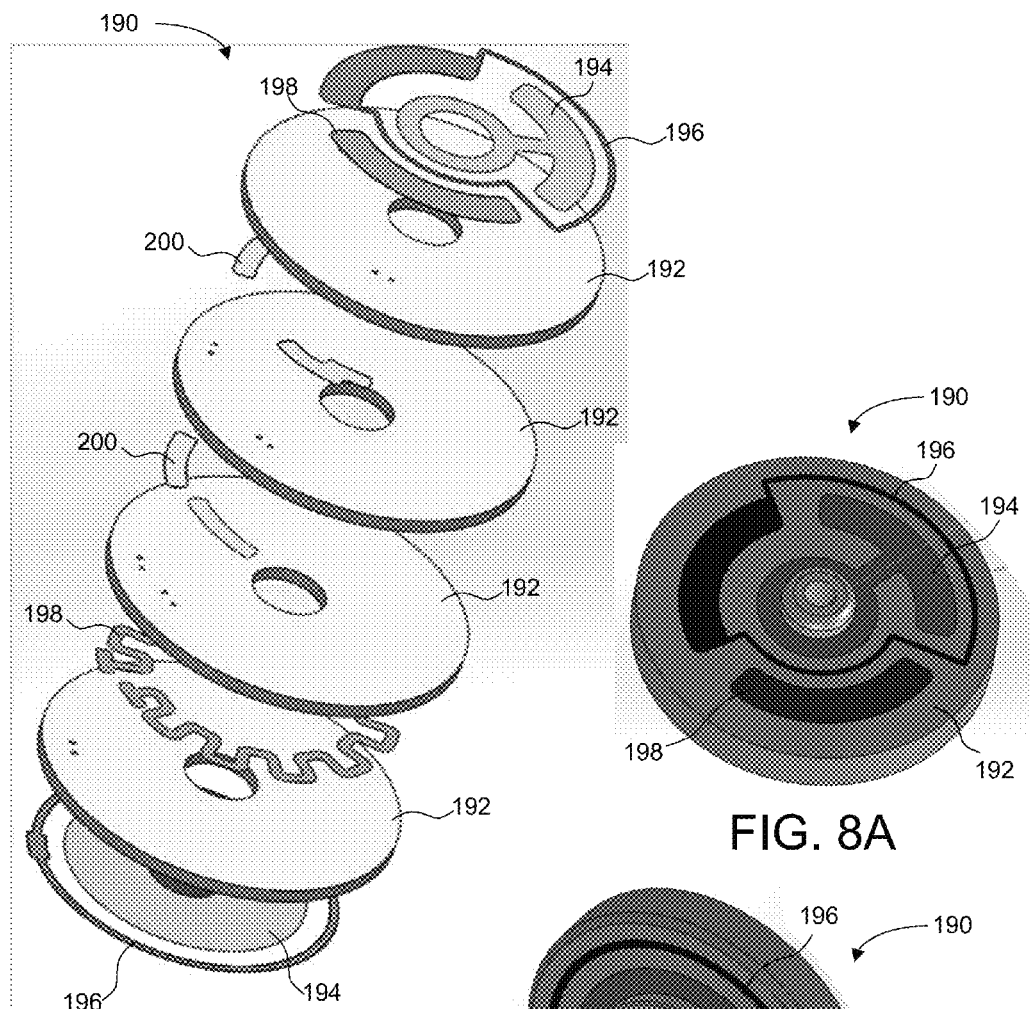
FIG. 7
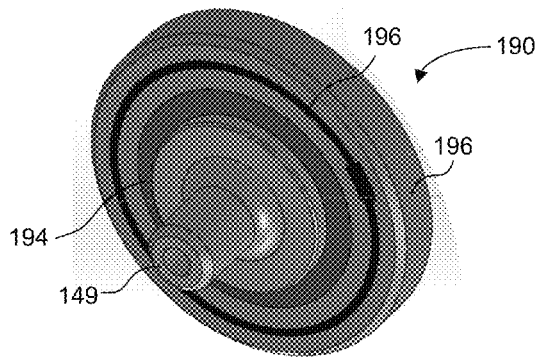
FIG. 8A
FIG. 8B

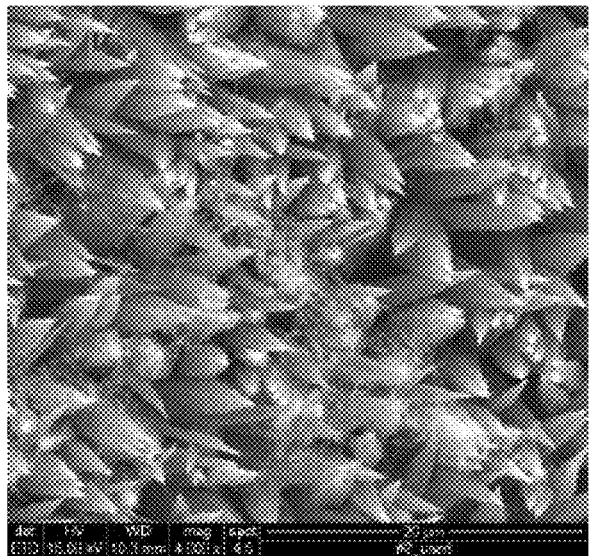
FIG. 11A
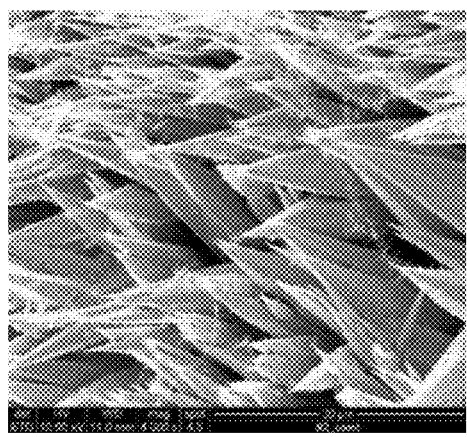 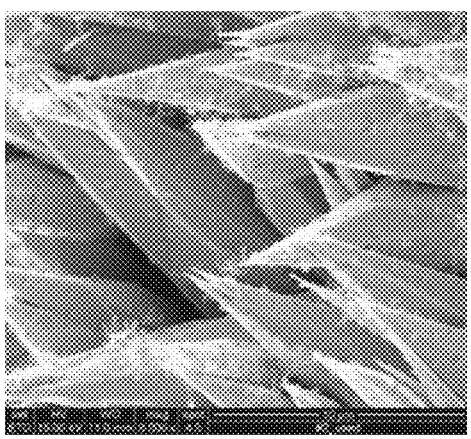
FIG. 11B       FIG. 11C

AGGLOMERATION AND CHARGE LOSS SENSOR WITH SEED STRUCTURE FOR MEASURING PARTICULATE MATTER

CROSS-REFERENCE TO RELATED APPLICATIONS

This application is a divisional of U.S. application Ser. No. 13/853,890, which is a continuation-in-part of U.S. application Ser. No. 13/315,146, which claims the benefit of U.S. Provisional Application No. 61/490,528, filed on May 26, 2011. Each of these applications is incorporated by reference herein in its entirety.

BACKGROUND

Internal combustion engines (e.g. diesel engines) typically generate an exhaust flow that contains varying amounts of particulate matter (PM). In general, particulate matter is small particles of solid matter (i.e., soot) that are suspended in exhaust gasses. The amount and size distribution of particulate matter in the exhaust flow tends to vary with engine operating conditions, such as fuel injection timing, injection volume, injection pressure, or the engine speed to load relationship. Adjustment of these conditions may be useful in reducing particulate matter emissions and average particle size in the particulate matter from the engine. Reducing particulate matter emissions from internal combustion engines is environmentally favorable. In addition, particulate matter measurements for diesel exhaust is useful for on-board (e.g., mounted on a vehicle) diagnostics of PM filters and reduction of emissions through combustion control.

On-board (in situ) sensors for particulate matter typically fall into two categories:
1. Accumulative sensors
2. Real-time sensors Accumulative sensors make use of the effect that exhaust particulates, especially soot particulates, tend to stick to surfaces exposed to exhaust gas. In an accumulative sensor, soot is allowed to accumulate on an exposed surface as a layer. A property of that soot layer is measured, either by vibrating the body (of which the surface is part) at its resonance frequency and then measuring the resonance frequency change that results from the accumulation of soot, or by measuring the resistance of the accumulated soot or its capacitance. When a certain threshold of the measured quantity is reached, the accumulation surface is heated to a high temperature to burn off the accumulated soot and the accumulation process starts anew. The frequency of repetition of this process is then used as a measure of the average particulate (or soot) content of the exhaust gas. Accumulative sensors are simple in construction, small enough to be installed like other exhaust sensors and relatively inexpensive. However, they have, due to their operating principle, a relatively slow response speed (not real-time) and suffer reliability issues when particles are accumulated that cannot be readily burned off.

Real-time sensors have response speeds in the millisecond range and typically make use of electrostatic effects on particulates, or use optical effects.

These sensors fall into four categories:
a. Natural charge detectors
b. Ionizing induced charge sensors
c. Contact charge sensors
d. Optical sensors Natural charge detectors try to detect the natural charge of particles produced during the production process. These sensors require very sensitive charge electronics and suffer from the fact that the natural charge of particles and/or their polarity can change on their way through the exhaust system.

Ionizing induced charge sensors create ions in the exhaust gas path through the sensor using a very high voltage on an electrode of a high surface curvature, like a thin wire or needle tip. Voltages are typically in the 2-15 kV range. This voltage causes a corona discharge in the particle carrying gas. Soot particles flowing through the corona discharge field acquire an electric charge. These charged particles are then collected by a collection electrode and the charge transfer rate of the collection electrode is measured. The collection electrode and the necessity to prevent charged gas ions to also transfer a charge to the collection electrode requires a fairly large and complicated apparatus that cannot be easily reduced to the size of a typical exhaust sensor.

Contact charge sensors typically use much lower voltages than ionizing induced charge sensors. In contact charge sensors soot particles coming in contact with a high voltage electrode acquire a surface charge that is determined by the surface charge density of the high voltage electrode. Typical voltages for the high voltage electrode are in the 500V to 3 kV range. These charged particles then deposit their acquired charge to grounded parts of the exhaust system or to a secondary detection electrode. The charge loss from the high voltage electrode is typically proportional to the particle concentration in the exhaust gas and is measured. However, because the resulting current (charge transfer per second) is very small, it is very difficult to isolate the high voltage electrode sufficiently to prevent current leakage. Any current that flows through an imperfect isolation to ground also creates a charge loss on the high voltage electrode and therefore causes a false sensor signal. As a way around that problem, a second collection electrode, essentially at ground voltage level, is placed in close proximity to the high voltage electrode and the charge accumulation on that electrode is measured. However, this necessitates an additional electrical connection that has to be well insulated from the high voltage supply to the electrode. For the typical temperatures encountered in the exhaust system of internal combustion engines it is very hard to find insulating materials that can withstand those temperatures and still maintain the high electrical insulating properties required.

The current detected by contact charge sensors is proportional to the particle content of the exhaust gas, but also proportional to the area of the electrodes. For the areas possible for a typically sized exhaust sensor the currents are in the low picoAmpere range for the typically encountered soot levels, which are very difficult to detect in the electrically noisy environment where internal combustion engines operate. Furthermore, the low currents require the use of electrometer grade amplifiers to detect and amplify the sensor signal. Due to limitations of current semiconductor technology, these amplifiers typically can maintain their specifications only over a narrow temperature range, which is much smaller than the typical temperature range required for vehicular applications (typically −40 to +125 degrees Celsius).

Optical sensors consist of a light source and a light detector. They measure either the opacity of the gas stream containing particles or measure light that is scattered by particles in the light path of the light source.

Common to all described real-time sensor methods is that soot accumulation on the sensor parts has a detrimental effect on the sensor performance and it is attempted to be remedied by various methods, depending on the embodiment. Either by diluting the exhaust gas with clean air, flowing compressed filtered air periodically past the electrodes (or optical parts in case of optical sensors) to blow off accumulated particles, or by heating the electrodes (or lenses in case of optical sensors) to a temperature where accumulated soot particles burn off, but not high enough to burn contacting soot particles immediately.

Further common to the described real-time sensors is that they have reaction times in the low millisecond range and can therefore for example detect changes in the soot concentration of the exhaust gas on a cylinder by cylinder basis for internal combustion engines.

Because of the above described limitations of the state-of-the-art particulate sensors for in-situ applications there is a need for a sensor that overcomes some of the limitations.

The sensor described in this invention combines certain aspects of the accumulative and the contact charge sensors in such a way as to increase the measured current by several orders of magnitude compared to a contact charge sensor, and by requiring soot accumulation on the electrodes to operate.

This allows this sensor to be scaled to the size of a typical exhaust sensor and makes it possible to use common insulators for the electrodes. In addition the sensor described in this invention does not require any special remedies to prevent soot accumulation on the sensing electrode. Compared to other real-time sensors, the sensor described in this invention has a slower response time, typically slower than 100 milliseconds, but faster than 5 seconds, which is sufficient for most applications.

SUMMARY

Embodiments of an apparatus are described herein. In one embodiment, the apparatus includes a sensor to measure particulate matter in an exhaust gas. An embodiment of the sensor includes an electrode and a seed structure. The electrode is configured to measure current due to movement of particulate matter relative to the electrode. The seed structure is deposited on the electrode during manufacturing or otherwise prior to use of the electrode. The seed structure includes a plurality of elongated members extending outward from the surface of the electrode. The elongated members are configured to promote charge transfer to the particulate matter during operation of the sensor. The charge transfer may be to particles and/or agglomerates of the particulate matter. In one embodiment, the seed structure includes dendric rhenium disposed on the surface of the electrode. In another embodiment, the seed structure includes nano-wires disposed on a surface of the electrode. Other embodiments may include other types of elongated members with similar size, geometry, chemical properties, and/or other features similar to dendric rhenium or nano-wires. Other embodiments of the sensor are also described.

Embodiments of methods are also described herein. In one embodiment, a method for making a sensor includes providing an electrode for measuring current due to movement of particulate matter relative to the electrode. The method also includes depositing a seed structure on the electrode. The seed structure includes a plurality of elongated members extending outward from the surface of the electrode. The elongated members are configured to promote charge transfer to the particulate matter particles and/or agglomerates during operation of the sensor.

In another embodiment, a method for using a sensor includes passing exhaust by an electrode having a seed structure deposited thereon. The seed structure includes a plurality of elongated members extending outward from the surface of the electrode. The elongated members are configured to promote charge transfer to the particulate matter during operation of the sensor. The method also includes measuring current due to movement of particulate matter relative to the electrode. The method also includes correlating the measured current to a quantity of the particulate matter in the exhaust. Other embodiments of methods are also described.

BRIEF DESCRIPTION OF THE DRAWINGS

FIG. 7 depicts an exploded view of one embodiment of a heater assembly for use in a sensor assembly such as the sensor assembly of FIG. 2D.

FIG. 8A depicts a perspective side view of an assembled embodiment of the heater insulator assembly of FIG. 7.

FIG. 8B depicts another perspective side view of an assembled embodiment of the heater insulator assembly of FIG. 7.

FIG. 11A depicts an enlarged view of one embodiment of the seed structure of FIG. 10.

FIG. 11B depicts an enlarged view of another embodiment of the seed structure of FIG. 10 having additional particle depositions connected to the seed structure.

FIG. 11C depicts a further enlarged view of the seed structure of FIG. 11B.

Throughout the description, similar reference numbers may be used to identify similar elements.

DETAILED DESCRIPTION

Figure 1:
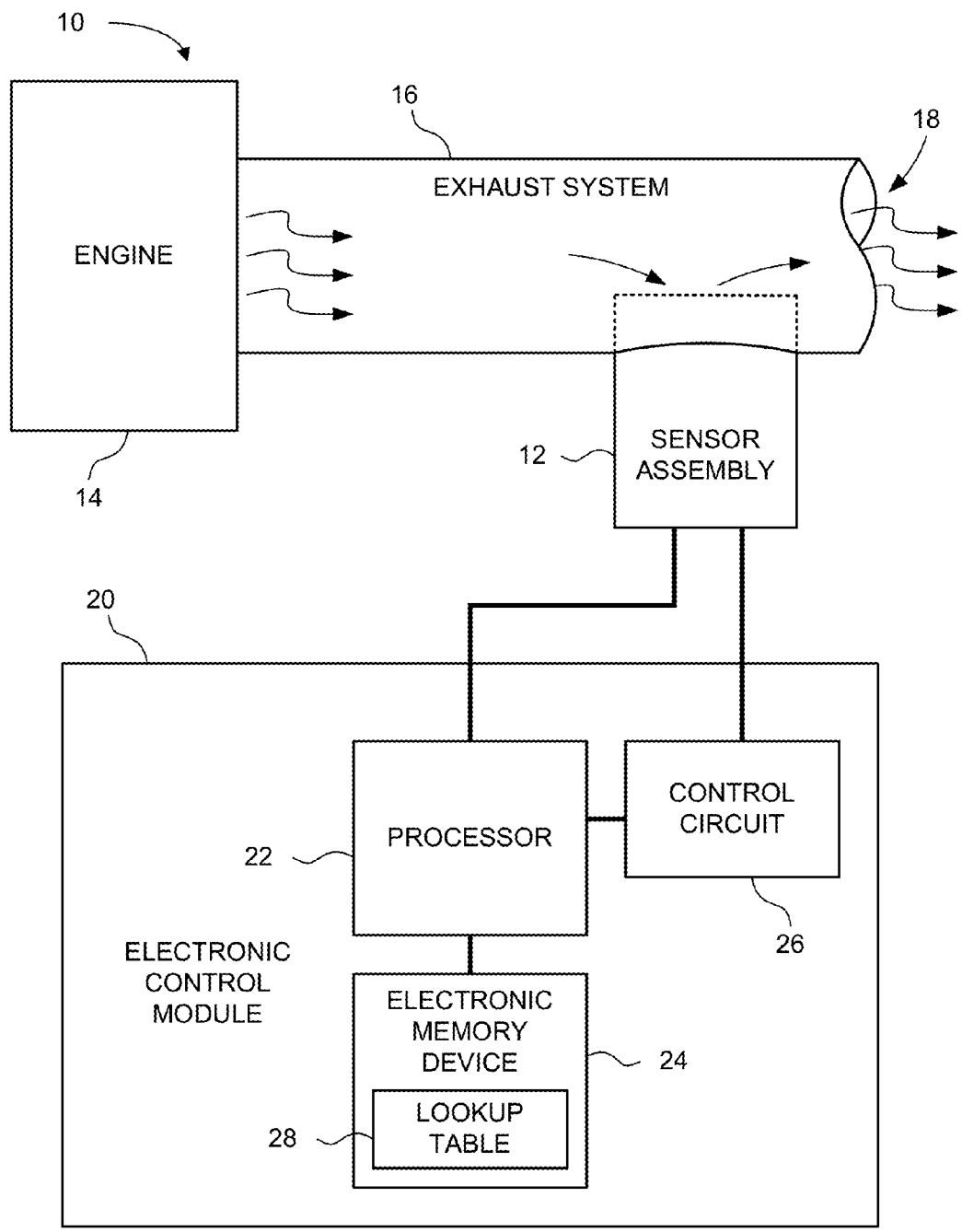
FIG. 1 depicts a schematic block diagram of one embodiment of an exhaust sensor system.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope. Reference throughout this specification to features, advantages, or similar language does not imply that all of the features and advantages that may be realized with the present invention should be or are in any single embodiment of the invention.

Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

The described embodiments include a particulate matter sensor that operates based on the agglomerated charge loss principle.

An exhaust stream containing small particles is directed toward an electrode connected to the positive connection of an insulated high voltage power supply. These particles will naturally attach themselves to the high voltage electrode and form a layer on that electrode. When, after a few minutes of operation, enough particles are attached, surface irregularities on the electrode and on the accumulated particle layer act as nucleation points where particles preferentially attach.

The time delay until which enough of a layer is formed depends on the particle concentration in the exhaust. Typically it is between 5 and 10 minutes for typical soot concentrations in the exhaust of a diesel engine. However, this time delay is relevant only for a new electrode that has never been exposed to exhaust gas. The soot layer initially formed will stay permanently on the electrode and can also be artificially created during the production process of the sensor to prevent this initial delay.

Because of the high electric field, and because the field strength, due to the physical geometry of the sensor, these particles attach preferentially to nucleation sites where the field strength is strongest, typically a surface imperfection or roughness element. Soot particles then continue to deposit in the presence of the electric field and form diffusion-limited aggregates (fractal or dendrite structures). Once the soot aggregates reach a large size (microns), dielectrophoresis may play a role whereby particles suspended in a fluid or gas will move toward the stronger field area in an inhomogeneous electric field, provided their relative permittivity is higher than that of the surrounding medium. The relative permittivity of soot or carbon is typically 5-10, while the relative permittivity of exhaust gas is close to 1. Soot or carbon particles comprise the majority of particles in the exhaust of an internal combustion engine at operating temperature.

When these soot particles attach to the nucleation points, they attach and are held there by intermolecular forces, like Van der Waals forces. Once they contact, and if they are at least partially conductive, they acquire the same surface charge as the electrode surface.

Because equal polarity charges repel, they are at the same time repelled by the electrode. However, for individual particles the electric field strength used in this sensor (400-1500 kV/m) is not strong enough to overcome the attachment forces.

However, because of the electric field, soot particles will agglomerate into branched filamentous 3-dimensional structures extending away from the electrode. Under the influence of the field these structures tend to self-organize such that they maximize their surface area as each individual branch of the structure acts as new nucleation and attachment point for new particles, but at the same time each branch is repelled by the other branches as they have equal charge and polarity. After some time such a structure acquires enough surface charge such that the resulting repelling electrostatic force between the structure and the electrode soot layer is enough to overcome the attachment force at the point where the structure is attached to the layer on the electrode, or in the structure where its attachment forces are weakest.

When these structures break off from the electrode, they carry part of the charge of the electrode with them and deposit their charge when they contact a grounded part of the sensor or the exhaust system. This charge deposition on the grounded part of the sensor can be detected as a current pulse flowing between electrode and ground, and is in this embodiment measured by a current meter between ground and the negative connection of the high voltage power supply.

Because of the self-organization of the branched structures in the electric field, these structures can carry a far higher charge per mass unit than individual particles can, given the voltages used. In the embodiment described here, the ratio of charge per mass unit is 100-1000 times higher than what would be expected from a charge transfer by individual particles as used in a contact charge sensor. Other embodiments may have different charge per mass ratios relative to the charge transfer by individual particles.

The surface to mass ratio is implied from the measurements of current, particle mass flow, and particle size and is a virtual expression for charge per mass unit acquired. The argument for high surface to mass ratio, or high surface charge density to mass ratio, is based on the fact that soot particles are conductive, therefore they can carry charge only on their surface.

During one example measurement, the mass concentration of particles was 6 mg/m$^3$ (particle mass per exhaust gas volume).

The measured particle count was about $6*10^7$ particles/cc and the average diameter of the particles was 50 nm. The measured current was about 41 nA, and the gas flow rate through the sensor was about 47 cc/second. This means about $2.82*10^9$ particles are flowing through the sensor with a total particle mass flow rate of about 282 ng/second.

The total surface area of the particles flowing through the sensor, assuming roughly spherical particles is therefore about $2.21*10^{-5}$ m$^2$/second. However, when they touch the electrode, what counts is not the total surface area of the particles, but roughly their cross sectional area. Therefore, the approximate effective area is only $5.5*10^{-6}$ m$^2$/second for spherical particles.

The effective surface to mass ratio of those particles is therefore about 19.5 m$^2$/g.

The surface charge density of the electrode with the described sensor at 1000V is about $6.9*10^{-5}$ Coulomb/m$^2$.

If each particle acquires from the electrode the same surface charge density as the electrode itself has, and transfers that charge, there would be a current of about $3.8*10^{-10}$ Coulomb/second or 0.38 nA. This can be expressed also as charge transferred per mass unit which would be in this case about $1.35*10^{-3}$ Coulomb/g.

In one embodiment, the current actually measured with the sensor is about 41 nA.

For a current of about 41 nA and assuming the agglomerates are acquiring the same surface charge density as the electrode, the total surface area of agglomerates transferring charge away from the electrode must therefore be about $5.9*10^{-4}$ m$^2$/second. Because the total particle mass flowing through the sensor is not changing, therefore the average effective surface to mass ratio for the agglomerates is about 2092 m$^2$/g.

Expressed as charge transferred per mass unit in this case comes to about 0.15 Coulomb/g. However it's expressed, there is typically more than a two orders of magnitude difference. Other embodiments may exhibit a difference between about 1.5-5 order of magnitude, or greater.

In operation, for a given particle concentration, an equilibrium is reached where the rate of break-off of agglomerated structures and their buildup balance. Higher soot concentrations will build structures faster, therefore creating more and larger current pulses.

A larger surface area of the electrode also creates more opportunity to create more structures and therefore creates more current pulses.

However, the surface area of the electrode has preferentially a positive curvature to create an inhomogeneous field. This physically limits the size of the electrode. Some embodiments may use multiple smaller curved electrodes to create a larger surface area.

The current pulses are integrated in the electronics and yield an average overall current that is proportional to the particle concentration of the flowing exhaust gas.

Increasing the voltage will create a higher surface charge density on the electrode and the agglomerating structures, yielding current pulses with higher average amplitude, but the limit of the voltage is the onset of ionizing discharge from the tips of the agglomerated structures, which would create a current from the electrode to ground that is not proportional to the soot concentration.

The magnitude of this voltage has to be experimentally determined, depending on the specifics of the embodiment.

Because of the far higher current, this measurement method has far lower demands on the electrical insulation properties of the electrode mounting than a contact charge sensor would need. In addition the sensitivity of the signal amplification circuit can be reduced such that it is possible, without expensive shielding, to deploy it in the electrically noisy environment of a vehicle.

FIG. 1 depicts a schematic block diagram of one embodiment of an exhaust sensor system 10. The illustrated exhaust sensor system 10 includes a sensor assembly 12, an engine 14, and an exhaust system 16. The engine 14 produces exhaust which moves through the exhaust system 16. The exhaust system 16 facilitates flow of the exhaust gases to a gas outlet 18, typically for emission into the atmosphere. The sensor assembly 12 is at least partially inserted into the exhaust system 16 to detect a parameter within the exhaust stream. As the gas in the exhaust system 16 passes over and/or through the sensor assembly 12, the sensor assembly 12 detects a condition within the exhaust by measuring chemicals or temperature or other parameters at the sensor assembly 12, as described herein. In a specific embodiment, the sensor assembly 12 includes a particulate matter sensor to detect conditions indicative of the presence of particulate matter within the exhaust stream.

The exhaust sensor system 10 also includes an electronic control module 20. The electronic control module 20 includes a processor 22, and an electronic memory device 24. The electronic control module 20 also may include a control circuit 26 to control some or all of the operations of the sensor assembly 12. Alternatively, some or all of the control circuit 26 functionality may be implemented at the sensor assembly 12 or at another location that is not necessarily proximate the electronic control module 20. Additionally, in some embodiments, the control circuit 26 may control a peripheral system (not shown). Some examples of peripheral systems that may be implemented at the sensor assembly 12 include, but are not limited to, a heater (not shown) or a chemical neutralizer system (not shown). Instead of or in addition to the chemical neutralizer system, some embodiments may include an emission control element (not shown) to neutralize other aspects of the chemicals and/or substances within the exhaust system 106, either upstream or downstream from the sensor assembly 10. In other embodiments, the control circuit 26 may control peripheral systems at other locations within the exhaust sensor system 10.

In one embodiment, the sensor assembly 12 relays a sensor signal to the processor 22 of the electronic control module 20. The processor 22 analyzes the sensor signal from the sensor assembly 12. If the sensor signal is corrupted, the processor 22 may send a control signal to the control circuit 26, for example, to shut down the sensor assembly 12. In this situation, or in other situations, the control circuit 26 may activate one or more heaters inside of or within proximity to the sensor assembly 12 to burn off particulate matter deposits that might corrupt the sensor signal from the sensor assembly 12. In some embodiments, the processor 22 sends the control signal to the control circuit 26 to activate a chemical injection system to introduce a chemical agent into the exhaust system 16 to remove particulate matter deposits built up on the sensor assembly 12. Further functionality of embodiments of the control circuit 26 is described below.

If the sensor signal from the sensor assembly 12 is not corrupt, the processor 22 may compare the sensor signal with data stored in a lookup table 28 on the electronic memory device 24 to determine one or more qualities of the exhaust in the exhaust system 16. For example, the processor 22 may determine an amount of particulate matter in the exhaust stream. The processor 22 also may compare the sensor signal from the sensor assembly 12 with data from the lookup table 28 to estimate, for example, a mass concentration of particulate matter in the exhaust stream. In other embodiments, the electronic control module 20 facilitates detection of one or more other qualities of the gas in the exhaust system 16. For example, types of sensors that may detect qualities of the exhaust stream may include but are not limited to, a particulate matter sensor, an oxygen sensor, a thermal sensor, an ammonia sensor, a flow rate sensor, and an air-fuel ratio sensor.

It should also be noted that embodiments of the sensor assembly 10 may be tolerant of fluctuations of certain gaseous constituents in a gas environment. In this way, the sensor assembly 10 may be calibrated to measure particular chemicals, materials, or other conditions within an exhaust stream, with relatively little or no disruption from one or more other chemical substances and/or operating conditions.

It should also be noted that the sensor assembly 12 may be used, in some embodiments, to determine a failure in another component of the exhaust sensor system 10. For example, the sensor assembly 12 may be used to determine a failure of a particulate matter filter (not shown) within the exhaust system 16. In one embodiment, a failure within the exhaust sensor system 10 may be detected by an elevated signal generated by the sensor assembly 12. In some embodiments, the exhaust sensor system 10 includes an alarm to indicate a detected failure of the sensor assembly 12 or other component of the exhaust sensor system 10. In some embodiments, the sensor assembly 12 also could be coupled to another sensor or detector such as a mass flow meter.

Figure 2A:
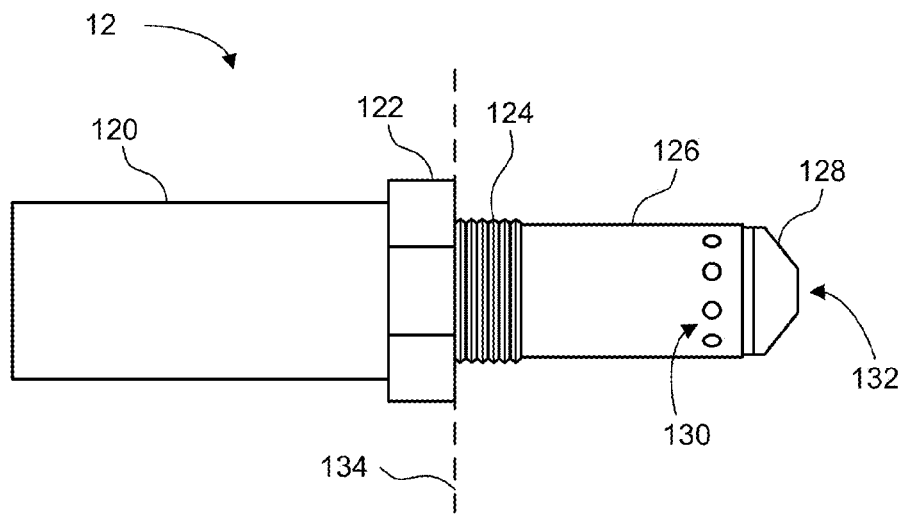
FIG. 2A depicts a schematic diagram of an exterior of one embodiment of the sensor assembly of FIG. 1.
Figure 2B:
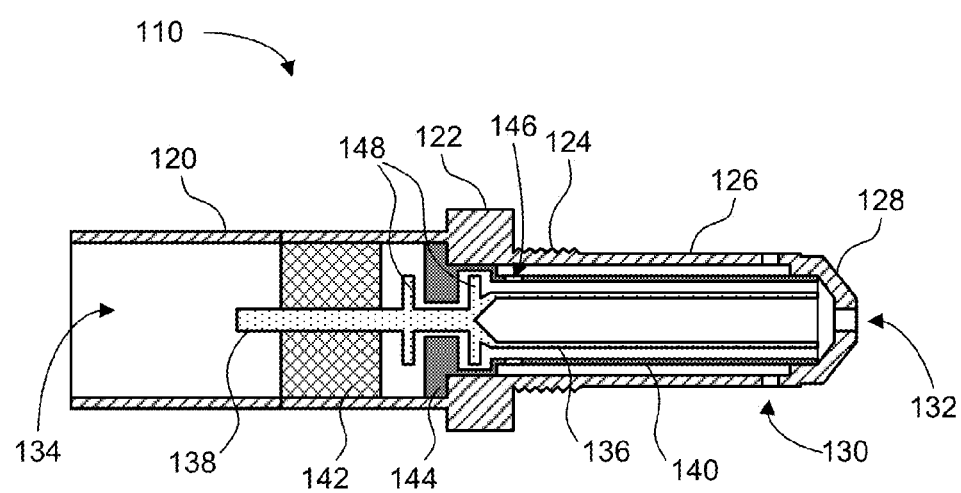
FIG. 2B depicts a schematic diagram of an interior of one embodiment of the sensor assembly of FIG. 1.
Figure 2C:
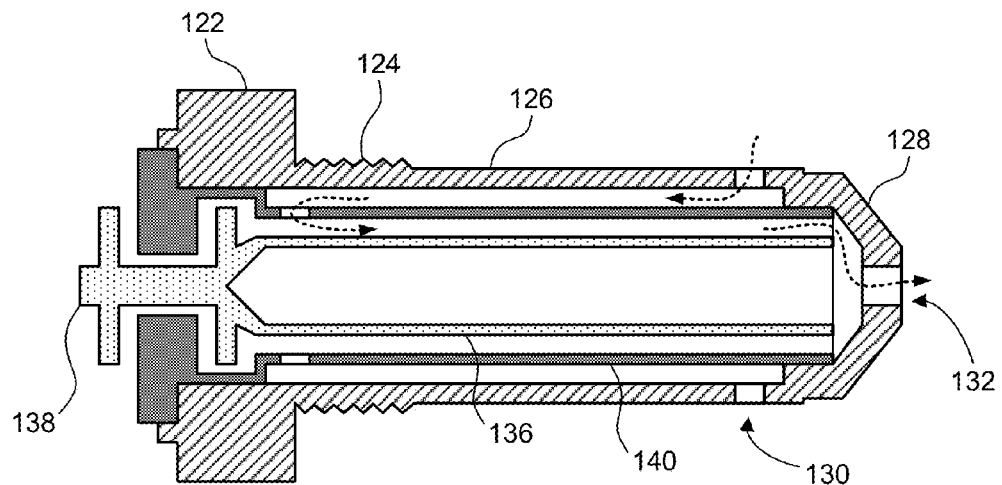
FIG. 2C depicts a schematic diagram of a flow pattern through the interior of the sensor assembly of FIG. 2B.

FIG. 2A depicts a schematic diagram of an exterior of one embodiment of the sensor assembly 12 of FIG. 1. FIG. 2B depicts a schematic diagram of an interior of one embodiment of the sensor assembly 12 of FIG. 2A. The illustrated external components of the sensor assembly 12 include a sensor housing 120, an intermediate bolt portion 122, and a threaded portion 124. The depicted external components also include an outer housing 126 with a cap 128. The outer housing 126 has one or more holes 130 which provide airflow within the outer housing 126. The cap 128 includes a separate opening 132 to facilitate the airflow within the outer housing 126. One example of an airflow pattern through the outer housing 126 of the sensor assembly 12 is shown in FIG. 2C and described in more detail below.

For reference, the sensor assembly 12 is installed within the exhaust sensor system 100 so that the sensor housing 120 and the bolt portion 122 of the sensor assembly 12 are typically outside of the exhaust stream through the exhaust system 106. The outer housing 126 and the cap 128 of the sensor assembly 12 are installed within the exhaust stream that passes through the exhaust system 106. The dashed line 134 distinguishes, generally, between the parts of the sensor assembly 12 that are outside (left of the dashed line 134) of the exhaust system 106 and the parts of the sensor assembly 12 that are inside (right of the dashed line 134) of the exhaust system 106. In one embodiment, the threaded portion 124 allows the sensor assembly 12 to be threaded, or screwed, into a corresponding hole within the exhaust system 106. Some of the threaded portion 124 may remain outside of the exhaust system 106 or, alternatively, may enter into the exhaust system 106. Many of the external components of the sensor assembly 12 may be made from metals, such as stainless steel, that are substantially insensitive to typical mechanical and/or chemical conditions within the exhaust sensor system 100.

In one embodiment, as exhaust gasses flow by the cap 128, the associated Venturi effect creates a low pressure which draws exhaust gas out of the interior of the outer housing 126. A corresponding amount of exhaust gas is drawn from the ambient exhaust stream through the holes 130 into the outer housing 126. Drawing a portion of the ambient exhaust stream into the outer housing 126 allows a sensor electrode 136 to measure the amount of particulate matter (PM) within the exhaust stream.

In one embodiment, the large surface area of the electrode 136 is cylindrically shaped. The cylinder can be hollow for weight reduction. The axis of the cylinder may be coincident with the axis of the electrode mounting stem 138.

FIG. 2B shows the inner construction of one embodiment of the sensor assembly 12. The inner construction of the sensor assembly 12 includes the sensor electrode 136 and the electrode mounting stem 138, as well as an inner baffle 140 and one or more insulators 142 and 144. In the depicted embodiment, the electric field extends radically between the surface of the electrode 136 and inner baffle 140. Because the electrode 136 has a smaller outside diameter than the inside diameter of inner baffle 140, the electric field is stronger at the surface of the electrode 136. In general, exhaust gas passing by the sensor assembly 12 enters into the outer housing 126 through the exhaust inlet holes 130. The exhaust gas flows through the space between inner baffle 140 and the outer housing 126 to one or more baffle holes 146 at the base of the inner baffle 140. The gas then flows in the space between cylindrical sensor electrode 136 and the cylindrical inner baffle 140 to the exhaust outlet 132 in the Venturi cap 128.

Because the flow of exhaust gas has to make a 90 degree turn when flowing from the holes 146 in the inner baffle into the space between the inner baffle 140 and the electrode 136, particles suspended in the gas stream are accelerated towards the electrode 136 because of their higher inertia compared to gas molecules. This flow pattern further supports the formation of particle agglomerates on the electrode 136.

In one embodiment, the inner baffle 140 is metallic and connected to the ground. The Venturi cap 128 is also connected to the inner baffle 140 and grounded.

Agglomerates that detach from the electrode 136 are repelled by the electrode 136 due to having equal charge and are attracted by the surface of the inner baffle 140, which has an opposite surface charge to the electrode 136 or agglomerates. Because detached particle agglomerates flow with the gas stream between inner baffle 140 and electrode 136, and because the gas stream has to execute two more turns to exit through the Venturi hole 132, these turns in the flow further insure that even agglomerates that have not deposited their charge in the inner baffle 140 are accelerated by their inertia towards a grounded surface part of the Venturi cap 128.

The grounded filter baffle 144 and the high voltage filter baffles 148, which are disk shaped, provide a tortuous path for particles that could migrate to the electrode insulator 142. The electric field between these filter baffles is highly inhomogeneous at the inner edge of filter baffle 144 and at the outer edges of filter baffles 148. Therefore, any particulates that migrate along the path between those filter baffles are attracted to these filter baffles themselves and will attach there. The normal gas flow path through the sensor insures that there will not be enough soot particles migrating to create large structures. The filter baffles therefore slow down particle accumulation on the insulator 142. Particle accumulations on the insulator 142 could form an electrically conductive path that will create a charge loss from electrode 136 to the sensor housing 120, parallel and in addition to the charge loss by particle agglomerates, which could detrimentally affect sensor performance. In addition, in some embodiments, the insulator 142 could be periodically heated by an embedded heater (not shown) such that any accumulated soot particles on the surface of the insulator 142 are burned off.

In some embodiments, this burn-off of soot particles may be implemented infrequently. Even in exhaust gas with particle concentrations far above the legal limit for emissions, the burn-off may be required only every few hours of operation.

Figure 2D:
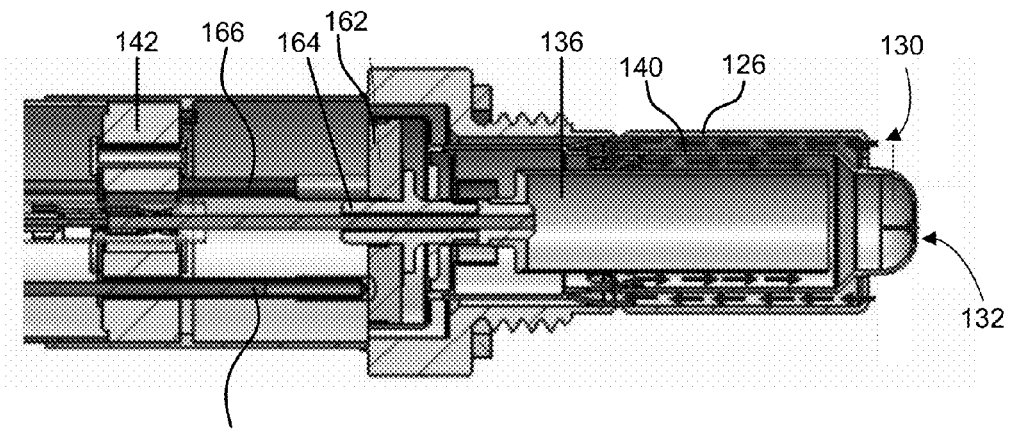
FIG. 2D depicts a schematic diagram of another embodiment of the sensor assembly of FIG. 1.

FIG. 2D depicts a schematic diagram of another embodiment of the sensor assembly 12 of FIG. 1. In contrast to the sensor assembly of FIG. 2B, the sensor assembly of FIG. 2D includes a heater assembly 162 (also referred to as a heater disk 162). The heater assembly 162 may perform some or all of the insulating functions of the insulator 144 of FIG. 2B. Additionally, the heater assembly 162 may perform one or more of the heater functions described herein. A more detailed depiction of the heater insulator assembly 162 is shown in FIGS. 7, 8A, and 8B and described in more detail below. The illustrated sensor assembly of FIG. 2D also includes a heater bushing 164, and separate electrical leads 166 and 168 for the heater and ground traces (see FIGS. 7, 8A, 8B). In general, the heater may be controlled to provide heat to the adjacent electrically insulating surfaces so as to burn off deposited particles that may have settled on or otherwise coupled to the insulating surfaces. Additionally, the heater supply heat to the sensor electrode 136, or a portion thereof, to burn off some or all of the soot or deposited particles at the heated location(s). The heater bushing 164 provides an insulated pathway for the corresponding portion of the sensor electrode 136 to pass through the heater insulator assembly 162.

In operation, exhaust gas flowing past the Venturi tip 128 of the sensor assembly 2 creates a low pressure area at the tip. Flow through the sensor assembly 12 is also promoted by a positive pressure that is created at the "inlet holes" 130 because of the velocity head (velocity is reduced to zero at the inlet holes and velocity is converted to pressure at the inlet holes by Bernoulli's principle). The low pressure at the tip 128 combined with the positive pressure at the inlet holes 130 draw exhaust gas through the sensor in a reproducible manner. The exhaust gas flows up through the space between exhaust housing and inner baffle and through holes 146 in the inner baffle 140 into the space between inner baffle 140 and electrode 136 and back down towards the Venturi hole 132. Although different operating conditions may be achieved, on example of a model of the illustrated embodiment exhibits a free stream exhaust velocity of 14 m/s and an exhaust gas temperature (EGT) of 200 C. At these conditions, the velocity in the sensor is 0.34 m/s (Re=25), and the volumetric flow rate is 0.82 liters/minute.

In one embodiment, the sensor body, including the inner baffle 140, is grounded through the vehicle exhaust system to the vehicle ground (not shown). The cylindrical electrode 136 is held at a potential of approximately 1,000 V relative to ground. In the depicted embodiment, the electrode 136 and its connections are insulated with two alumina discs: the back insulator disk 142, which also acts as holder for the heater and guard connections, and the heater disk 162. The heater disk 162 also mechanically fixes the electrode 140 assembly in the sensor 12. In one embodiment, one or both of the insulator disks 142 and 162 are co-fired. In some embodiments, the heater disk 162 contains a platinum thick-film heating element (see FIGS. 7, 8A, 8B) that serves also as resistance temperature detector (RTD) for temperature measurements. The heater element can be used to evaporate moisture that condenses on the heater disk 162 during condensing conditions, and as mentioned above can also be used to burn off soot that accumulates on the exhaust side face of the heater disk 162 over time. Under some operating conditions the function of burning off soot may be used infrequently, as needed.

In one embodiment, the electrode 140 assembly is brazed to the heater bushing 164, which acts as the main insulator between the electrode 136 and heater disk 162. The hole in the heater disk 162 in which the heater bushing 164 is brazed is surrounded on both sides of the heater disk by metalized guard rings (see FIGS. 7, 8A, 8B). These guard rings are electrically connected to the brazing metal in the heater disk 162 (e.g., to a heater bushing braze joint) and connected to the "guard" connection 166. Similar guard rings may be implemented on one or both of the outermost surfaces of the heater disk 162 (See FIGS. 8A and 8B). These guard traces are further connected to the inner shield of a triaxial sensor supply cable (guard), while the inner conductor of the triaxial cable supplies the high potential for the electrode 136. The outer conductor of the triaxial cable is connected on the electronic side to ground to provide RF and capacitive noise shielding.

The electronics for the sensor 12 hold the guard connection at ground potential while the guard itself is connected to the negative side of the 1,000 V supply. Therefore, any current leakage through either the bulk resistivity of the heater bushing 164, or due to conducting surface contaminants on heater disk 162 or back insulator between the electrode 136 and the guard trace creates a current load on the HV power supply, but does not contribute to a current measured between the negative of the 1,000 V supply and ground.

Figure 3:
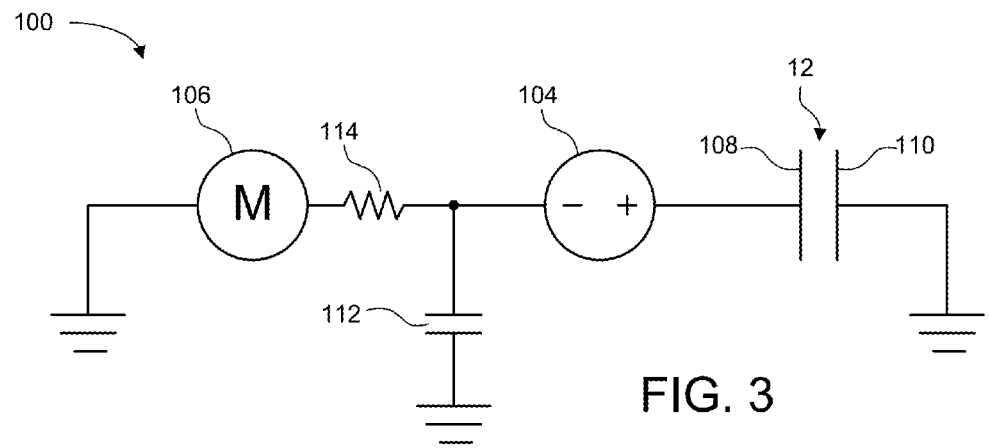
FIG. 3 depicts a schematic circuit diagram of one embodiment of the control circuit of FIG. 1.

FIG. 3 depicts an electrical schematic block diagram of one embodiment of the control circuit of FIG. 1.

The positive connection of the high voltage source 104 is connected to the electrode 108 of sensor assembly 12, while the inner baffle 140 and the rest of the sensor assembly 12 are connected to ground. This rest of the sensor assembly 12 is depicted as part 110 in the electrical schematic block diagram. The negative connection of the high voltage source 104 is connected to one side of the filter resistor 114 and to one side of the filter capacitor 112. The other side of filter capacitor 112 is grounded. The other side of the resistor 114 is connected to one side the current meter 106, and the other side of the current meter 106 is grounded.

The resistor 114 and filter capacitor 112 form a low pass filter with a bandwidth of, for example, 5-10 Hz. The current pulses created by the operation of sensor assembly 12 are integrated in this low pass filter.

Figure 4:
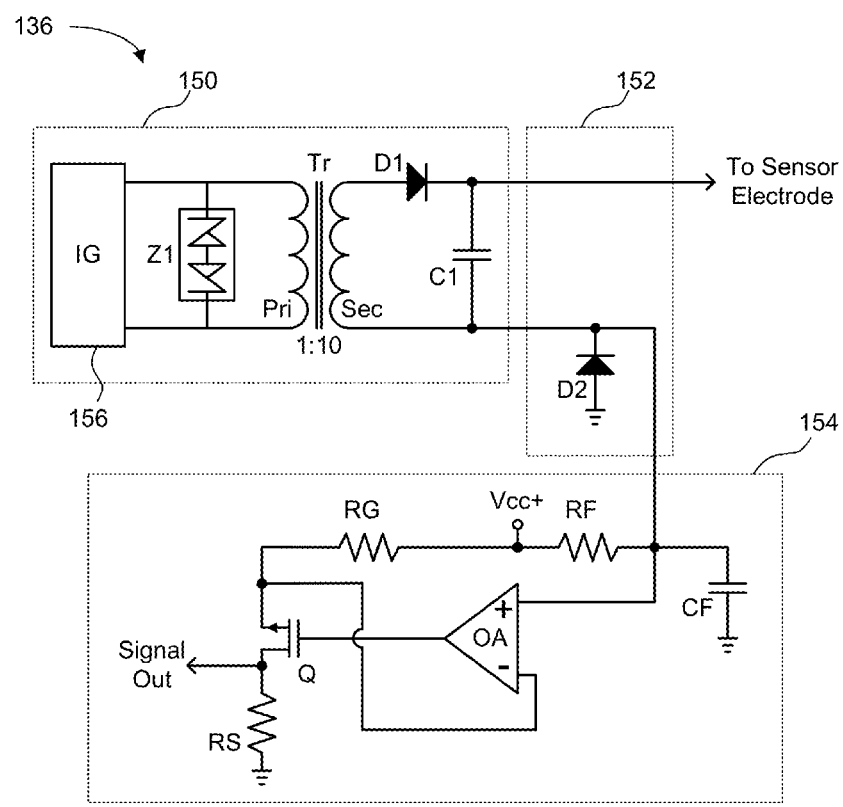
FIG. 4 depicts a schematic circuit diagram of another embodiment of the control circuit of FIG. 1.

FIG. 4 depicts a more detailed electrical schematic of the schematic block diagram depicted in FIG. 3. Generally, the illustrated control circuit 26 includes a generator block 150, a protection block 152, and a detection and filter block 154. Other embodiments may include fewer or more blocks and/or fewer or more components within one or more of the illustrated blocks.

In the depicted embodiment, the generator block 150 includes an impulse generator (IG), a bi-directional Zener diode (Z1), a transformer (Tr), a high voltage diode (D1), and a high voltage capacitor (C1). The illustrated transformer includes primary and secondary windings with a 1:10 winding ratio, although other embodiments may have different winding ratios. The protection block 152 includes the clamping diode D2. The detection block 154 includes an initial filter resistor (RF), an initial filter capacitor (CF), an operational amplifier (OA), a gain resistor (RG), a PMOS transistor (Q), and a current to voltage conversion resistor (RS).

In general, the control circuit 26 generates a relatively high voltage to apply to the sensor electrode 108 and, in turn, generates an output signal that can be correlated with the particulate matter level of the exhaust stream to which the sensor electrode 108 is exposed. Specifically the secondary side of the transformer TR, diode D1, and capacitor C1 form an embodiment of the floating voltage source 108 depicted in FIG. 3. While specific circuit components are shown in a particular arrangement, other embodiments may use similar or different circuit components to achieve the same or similar results. Additionally, while the illustrated circuit is implemented substantially in hardware, it may be possible to implement some portions of the control circuit 26 using software instructions that are executed by a central processor or other digital signal processing device.

In one embodiment, the impulse generator 156 generates periodic, short pulses duration (e.g., about 1-2 μsec) with a particular repeat rate (e.g., about 1400 impulses per second) and a maximum amplitude (e.g., about 1000V). These impulses charge the capacitor C1 to the same amplitude (e.g., about 1000V). The positively charged side of capacitor C1 is connected to the sensor electrode 108 of the sensor assembly 100. Agglomerates that get positively charged at the sensor electrode 108 carry away some of the capacitor charge periodically and, thus, discharge the capacitor C1 relative to the ground reference (e.g., vehicle ground). This discharge current flows through the initial filter resistor RF and are integrated at the initial filter capacitor CF. The operation amplifier OA together with the gain resistor RG and PMOS transistor Q form an inverting current amplifier with a gain of −RF/RG. This amplified current Tout flows out of the drain of PMOS transistor Q into the voltage conversion resistor RS. The voltage at resistor RS is therefore proportional to RS*Iout, according to Ohms law. Other methods of detecting the discharge current can be employed as well.

In one embodiment, the impulse generator 156 receives vehicle battery voltage (about 12V) and switches the vehicle battery voltage on the primary winding of the transformer until the current in this winding reaches a primary winding threshold value. In one embodiment, the primary winding threshold value is approximately 3 Amperes, although other embodiments may use a different primary winding threshold value. When the specified current limit is reached, the current is rapidly switched off. In one embodiment, the inductive flyback pulse of the primary winding is limited by the bidirectional Zener diode Z1 to a value of 100V. Because the transformer has a winding ratio of 10:1 between its secondary and primary windings, the flyback pulse limited to 100V on the primary side translates into a 1000V pulse on the secondary side. Although some embodiments may use 100V on the primary side and 1000V on the secondary side, other embodiments may use different voltages and/or different winding ratios.

The impulse generator 156 periodically switches the battery on to the primary winding to generate corresponding pulses on the secondary side on a regular basis. In one embodiment, pulses are generated once every 0.7 msec (1.4 kHz), although other embodiments may use a different pulse generation frequency.

The 1000V pulse on the secondary side of the transformer charges the high voltage capacitor C1 via the diode D1 to 1000V. This circuit is a flyback converter with primary voltage limiting.

The 1000V charge of the high voltage capacitor C1 is connected to the sensor electrode 108.

If soot agglomerates extend all the way from the sensor electrode 108 to the grounded part 110 of the sensor assembly, a short circuit would form that shorts the high voltage source to ground. This creates a high current that would discharge C1 rapidly while CF would be charged rapidly to a high negative voltage. The protection diode D2 prevents CF to be charged to a more negative voltage than about −0.7V. The high discharge current of C1 will heat up the particles of which the shorting soot agglomerate is formed to a high enough temperature to burn them. This way these types of short circuits are self extinguishing.

The negative side of high voltage capacitor C1 is connected to the initial filter resistor RF and initial filter capacitor CF. The filter capacitor CF integrates the current pulses caused by dislodged soot agglomerates as described before. Therefore the average current through RF is proportional to the charge loss rate from the electrode caused by dislodging soot agglomerates depositing their charge to a grounded part of the sensor or exhaust system. This integrated current is correlates with the soot concentration of the exhaust gas flowing through the sensor. Because of the need for integration of the current pulses, this sensors response time is determined by the low pass filter bandwidth of the low pass filter formed by RF and CF. For typical implementations, this bandwidth is less than 10 Hz.

Figure 5:
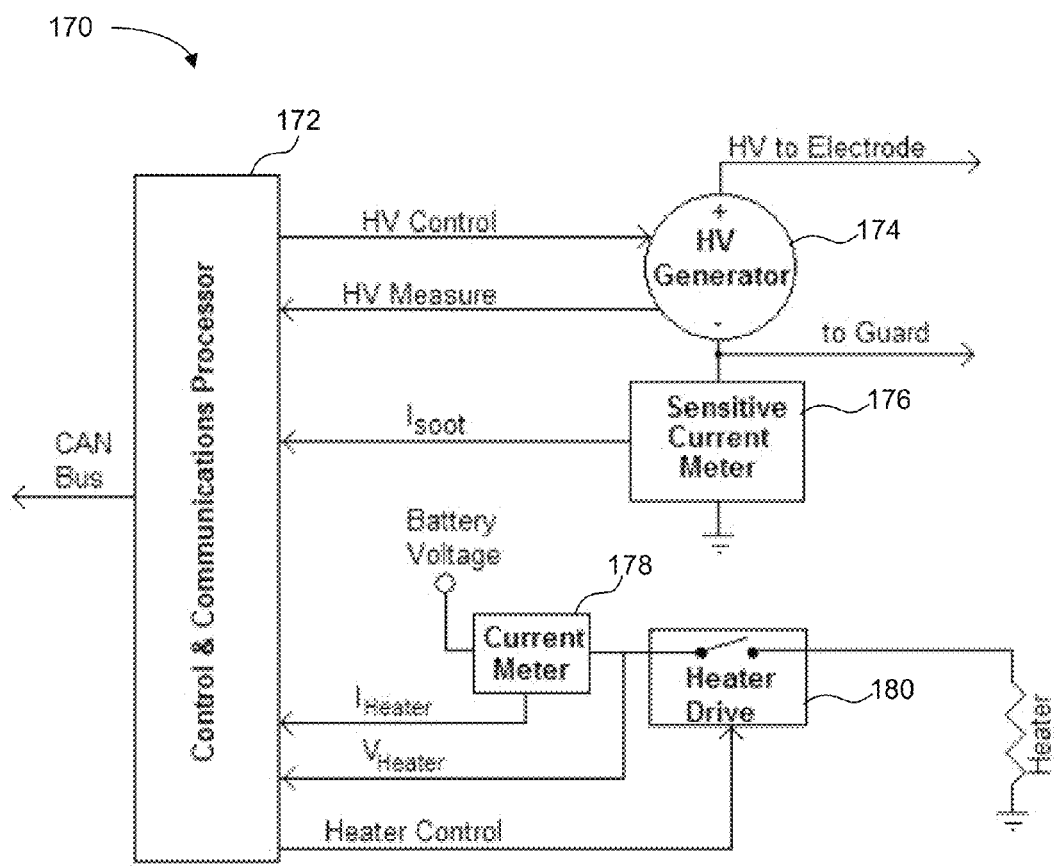
FIG. 5 depicts a schematic circuit diagram of the sensor assembly of FIG. 1.

The exhaust sensor system 10 also includes an electronic control module 20. The electronic control module 20 includes a processor 22, and an electronic memory device 24. The electronic control module 20 also may include a control circuit 26 control some or all of the operations of the sensor assembly 12. Alternatively, some or all of the control circuit 116 functionality may be implemented at the sensor assembly 12 or at another location that is not necessarily proximate the electronic control module 20. Additionally, in some embodiments, the control circuit 26 may control a peripheral system (not shown). Some examples of peripheral systems that may be implemented at the sensor assembly 12 include, but are not limited to, a heater (not shown) or a chemical neutralizer system (not shown). Instead of or in addition to the chemical neutralizer system, some embodiments may include an emission control element (not shown) to neutralize other aspects of the chemicals and/or substances within the exhaust system 106, either upstream or downstream from the sensor FIG. 5 depicts a schematic circuit diagram of the sensor assembly of FIG. 1. The illustrated circuit diagram includes a processor 172, a high voltage generator 174, a sensitive current meter 176, a current meter 178, and a heater drive 180 to control the heater. The illustrated circuit diagram also includes several control and/or communication lines. In one embodiment, the electrode 136 is connected to the positive side of the high voltage generator 174, and the guard trace is coupled to the negative side of the high voltage generator 174. Current measured by the sensitive current meter 176 may be reported to the processor 172, which can correlate the measured current to a characterization of the particulates in the exhaust gas to which the electrode 136 is exposed. More generally, the control and communications processor coordinates all measurements, does the analog to digital conversions, controls the operation of the HV generator, processes the data, and communicates the results via a CAN bus.

Figure 6A:
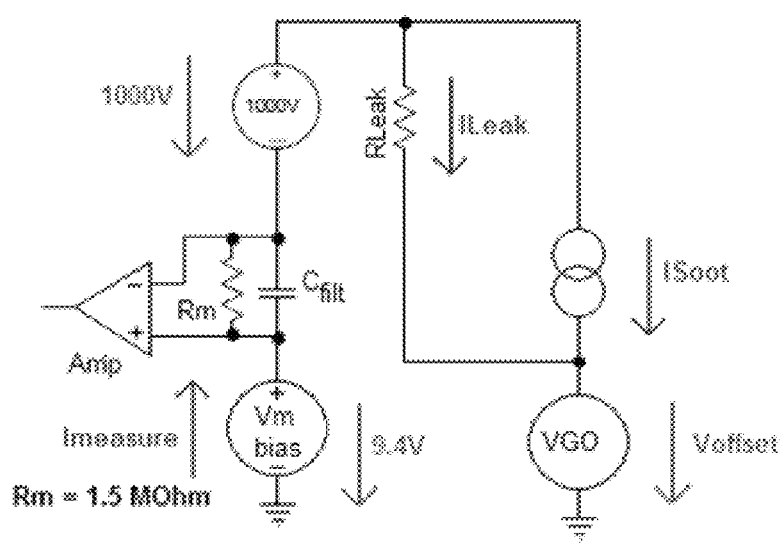
FIG. 6A depicts a schematic circuit diagram of one embodiment of a sensor assembly circuit.

FIG. 6A depicts a schematic diagram of one embodiment of a sensor assembly circuit 182. This embodiment of the sensor assembly circuit 182 does not include a guard trace. Generally, the current ISoot generated by the sensor represents the charge loss current from the sensor electrode 136. The resistance RLeak represents the leakage resistance between the electrode 136 and the sensor body 126, which is connected to the exhaust pipe (see FIG. 1). The voltage VGO represents a ground offset voltage between the exhaust pipe and the electronics ground. The measurement resistance Rm corresponds to a measurement current Imeasure. And the variable gain amplifier Amp amplifies the voltage drop over the measurement resistance Rm caused by the measurement current Imeasure. In this embodiment, the measurement current is the sum of the leakage current ILeak and the sensor current ISoot. In some embodiments, this arrangement requires a very large leakage resistance RLeak in order to avoid false positives (e.g., 1 TOhm for <0.25 mg/m$^3$ error).

Figure 6B:
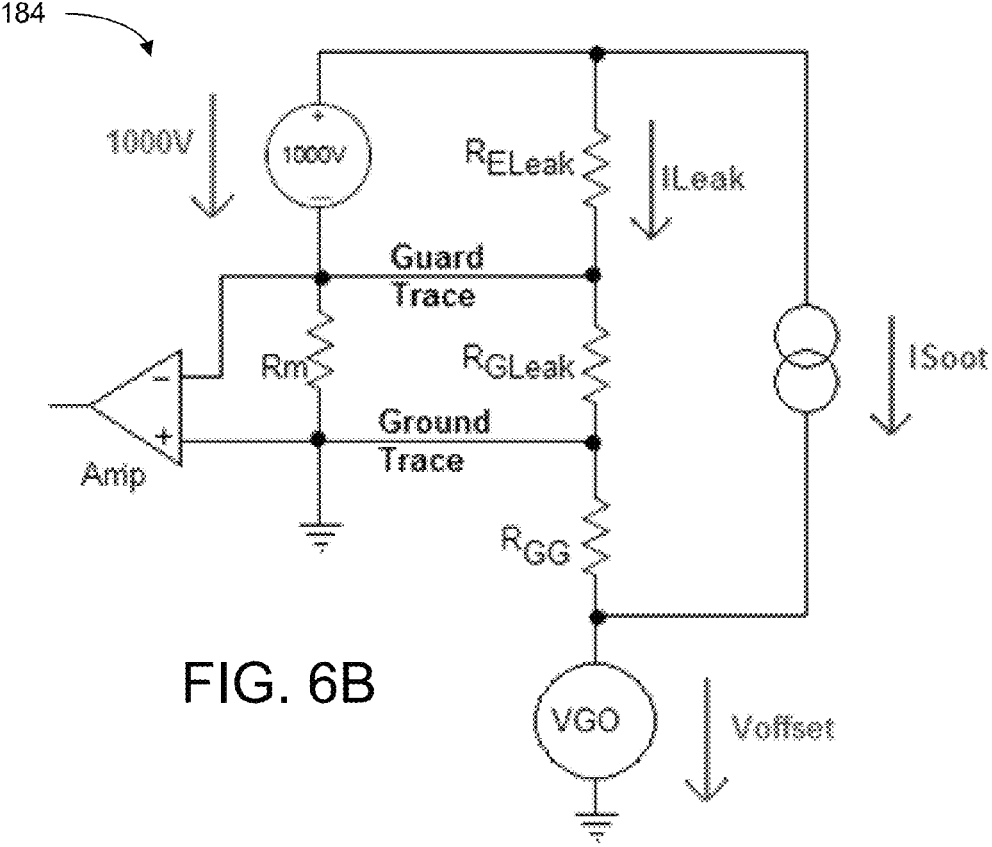
FIG. 6B depicts a schematic circuit diagram of another embodiment of a sensor assembly with a guard trace.

FIG. 6B depicts a schematic circuit diagram of another embodiment of a sensor assembly with a guard trace. The presence of the guard trace in the illustrated circuit divides the leakage current ILeak over three resistances, which include a first resistance released RELeak between the electrode 136 and the guard trace, a second resistance RGLeak between the guard trace and a ground trace, and a third resistance RGG between the ground trace and the sensor body 126 (and the connected exhaust pipe). The third resistance has no known impacts on the measurements of the sensor assembly.

The first resistance RELeak increases the load on the HV generator 174, while the sensor gain changes approximately linearly with the electrode voltage between about 800-2, 000V. Below about 800 MOhm for RELeak, the electrode voltage will drop. The calculated gain error is only about 5% relative to an RELeak of about 150 MOhm, and goes down to about 0% as the RELeak resistance value increases. In some embodiment, the electrode voltage may be monitored between two thresholds, and known or calculated error rates in the gain change for RELeak within that range may be compensated for. For example, gain changes for RELeak may be compensated for between about 40-800 MOhm.

The second resistance RGLeak is typically much larger than the measurement resistance Rm, so the impact of the second resistance RGLeak may be negligible for any values over about 100 kOhm. However, an input offset at the simplifier may create a false current through the second resistance RGLeak. Thus, an amplifier with a very low offset may be used. For example, the amplifier may have an offset of about 20-25 µV over the target temperature range.

FIG. 7 depicts an exploded view of one embodiment of a heater assembly 190 for use in a sensor assembly such as the sensor assembly 12 of FIG. 2D. The heater assembly 190 is substantially similar to the heater assembly 162 of FIG. 2D. The illustrated heater assembly 190 includes several layers of insulating materials 192 such as alumina. On the outer surfaces of the insulating layers 162, one or more ground traces 194 and one or more guard traces 196 are provided. The traces 194 and 196 may be any type of electrically conducting material (e.g., printed conductors) that is applied to the corresponding insulating surfaces. The heater assembly 190 also includes heater conductors 198 and 200, including one or more contact pad(s) and inner-layer inner-connect trace(s).

The ground trace 194 on the insulator layer 192 prevents ground offsets between the electronics ground and the sensor body ground. In some embodiments, the ground trace 192 may be electrically coupled to the ground side of the heater.

As explained above, the guard trace 196 effectively divides the leakage resistance RLeak into three separate resistances. This reduces errors that would otherwise occur due to the leakage current RLeak via bulk conductivity, surface contamination of the exposed insulating layers 192, or condensation on any insulator layer 192. The guard trace electrically extends through the system cabling via a shield conductor. In some embodiments, three-dimensional guard traces may be implemented within the sensor insulating layers to provide further protection.

FIG. 8A depicts a perspective side view of an assembled embodiment of the heater insulator assembly of FIG. 7. FIG. 8B depicts another perspective side view of an assembled embodiment of the heater insulator assembly of FIG. 7.

Figure 9:
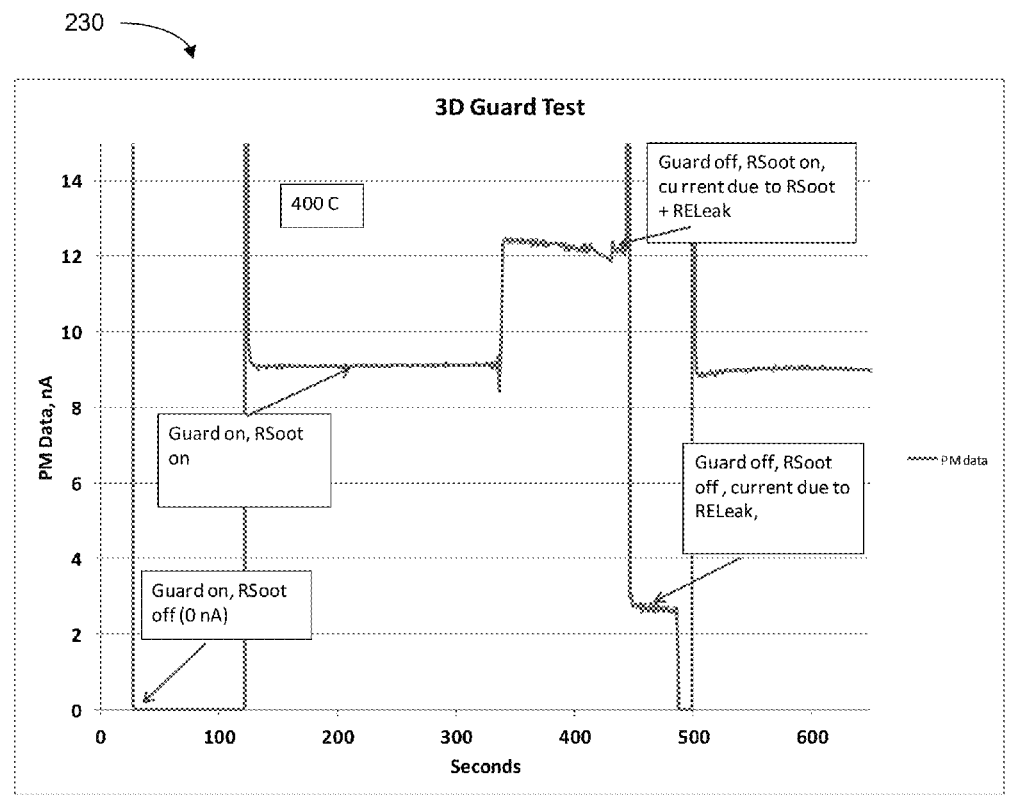
FIG. 9 depicts results from modeling of one embodiment of a sensor assembly circuit which includes a guard trace.

FIG. 9 depicts results from modeling of one embodiment of a sensor assembly circuit which includes a guard trace 196. This modeling was obtained from simulations performed with a test setup using an RELeak value of 10 GOhm, an RGLeak value of 40 MOhm (and down to 2.2 MOhm), and an RSoot value (representing the sensor) of 100 GOhm. The RELeak resistance exhibited about 100 nA leakage current, and the RSoot exhibited about 10 nA with the guard trace 196 present. This is compared with about 12 nA without the guard trace 196.

Figure 10:
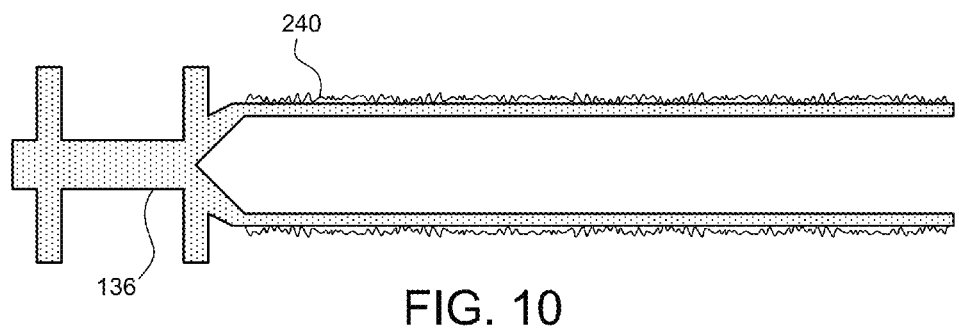
FIG. 10 depicts one embodiment of a sensor electrode with a deposited seed structure of, for example, dendritic rhenium.

FIG. 10 depicts one embodiment of a sensor electrode 136 with a deposited seed structure 240 of, for example, dendritic rhenium. A sensor electrode 136 that has not been operated previously may require, or benefit from, several minutes of operation in a gas stream containing particles to reach a constant output with acceptable sensitivity. Initially, the observed current may be close to zero, then rises rapidly to a value below the final sensitivity, and then rises slowly to the final sensitivity value. The timing of these changes in sensitivity are due, at least in part, to the cumulative charge transfer effect of particles depositing on the exposed surface of the electrode 136 and/or the corresponding surface of the inner baffle 140. Higher soot concentrations during this initial period cause a faster rise to the final sensitivity value. In some embodiments, coating the positive electrode 136 of the sensor 12 with a seed structure during manufacturing can accelerate the ability of particles to deposit on the exposed surface area during operation of the sensor 12. Dendritic Rhenium (dendrites in the micron scale) is one example of a seed structure that speeds up the startup process. In some embodiments, the use of dendritic rhenium may accelerate reaching final sensitivity by about 40-50%. In other embodiments, other types of seed structures may be used.

FIG. 11A depicts an enlarged view of one embodiment of the seed structure of FIG. 10. FIG. 11B depicts an enlarged view of another embodiment of the seed structure of FIG. 10 having additional particle depositions connected to the seed structure. FIG. 11C depicts a further enlarged view of the seed structure of FIG. 11B. In particular, FIGS. 11B and 11C illustrate field enhancement and preferential soot deposition primarily at the tips of dendritic rhenium.

Figure 12:
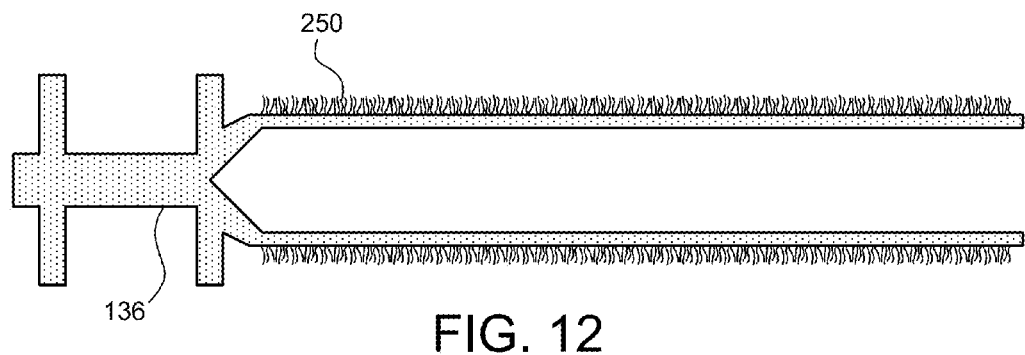
FIG. 12 depicts one embodiment of a sensor electrode with a coupled structure of nano-wires.
Figure 13:
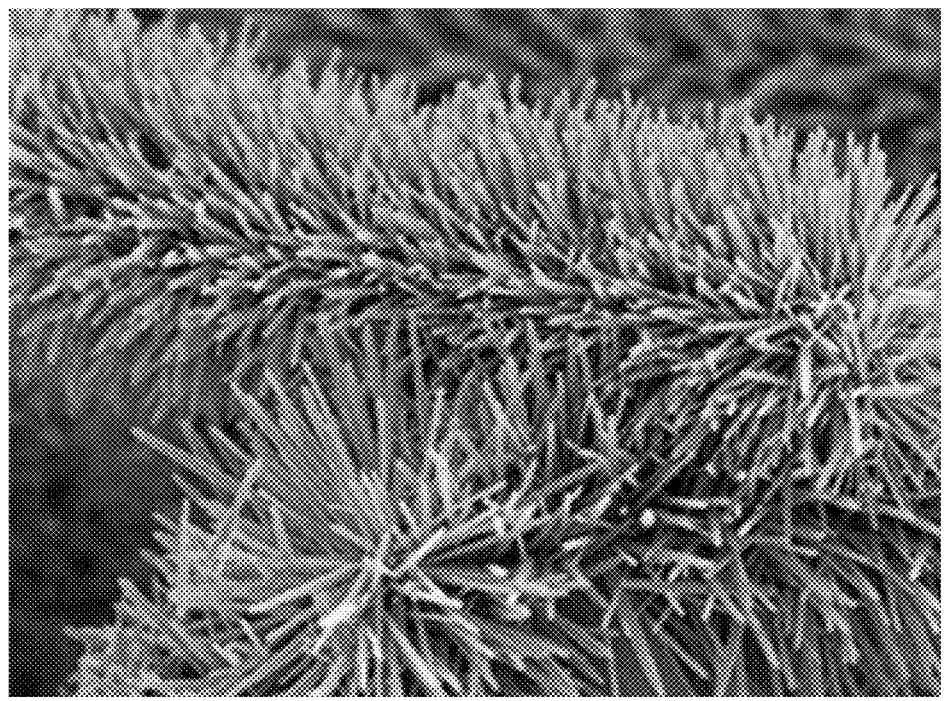
FIG. 13 depicts an enlarged view of another structure of nano-wires.

FIG. 12 depicts one embodiment of a sensor electrode with a coupled structure of nano-wires. In general, the nano-wires are characterized by material spacing and lengths of nano-wires in approximately the micron range, with tip diameters in approximately the sub-micron range. This coupled structure of nano-wires may serve as an alternative type of seed structure on the electrode 136 of the sensor. FIG. 13 depicts an enlarged view of another structure of nano-wires. In some embodiments, stable nano-wires are assembled during manufacturing. During operation, these nano-wires create the field enhancement to highly charge soot particles. In this type of assembly, the amplification does not necessarily come from agglomeration and breakoff of particles, but rather from the high charge between the nano-wire coated electrodes. In some embodiments, the field amplification at the tips of the nano-wires is chosen such that the repellant force experienced by a touching particle is always bigger than the intramolecular forces that allow a soot particle to stick to other materials like the nano-wires. The magnitude of the field amplification is determined by the length/radius ratio of the nano-wires and their spacing. In other embodiments, other factors may influence the design and implementation of the nano-wires. Additionally, other embodiments may utilize other nano-structures that are not necessarily classified as nano-wires.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A sensor comprising:
an electrode for measuring current due to movement of particulate matter relative to the electrode; and
a seed structure deposited on the electrode, wherein the seed structure comprises a plurality of elongated members extending outward from the surface of the electrode, wherein the elongated members are configured to promote charge transfer to the particulate matter during operation of the sensor, wherein the seed structure comprises nano-wires disposed on the surface of the electrode.

2. The sensor of claim 1, wherein the seed structure comprises dendric rhenium disposed on the surface of the electrode.

3. The sensor of claim 1, wherein the elongated members are configured to promote local charge concentration at tips of the elongated members to enhance a strength of a local electrical field.

4. The sensor of claim 1, wherein the elongated members are configured to promote an attraction of the particulate matter to tips of the elongated members.

5. The sensor of claim 1, wherein the elongated members are configured to promote charge transfer to particles of the particulate matter during operation of the sensor.

6. The sensor of claim 1, wherein the elongated members are configured to promote charge transfer to agglomerates of the particulate matter during operation of the sensor.

7. A method for making a sensor, the method comprising:
providing an electrode for measuring current due to movement of particulate matter relative to the electrode; and
depositing a seed structure on the electrode, wherein the seed structure comprises a plurality of elongated members extending outward from the surface of the electrode, wherein the elongated members are configured to promote charge transfer to the particulate matter particles and/or agglomerates during operation of the sensor, wherein the seed structure comprises nano-wires disposed on the surface of the electrode.

8. The method of claim 7, wherein the seed structure comprises dendric rhenium disposed on the surface of the electrode.

9. The method of claim 7, wherein the elongated members are configured to promote local charge concentration at tips of the elongated members to enhance a strength of a local electrical field.

10. The method of claim 7, wherein the elongated members are configured to promote an attraction of the particulate matter to tips of the elongated members.

11. A method for using a sensor, the method comprising:
passing exhaust by an electrode having a seed structure deposited thereon, wherein the seed structure comprises a plurality of elongated members extending outward from the surface of the electrode, wherein the elongated members are configured to promote charge transfer to the particulate matter during operation of the sensor, wherein the seed structure comprises nanowires disposed on the surface of the electrode;

measuring current due to movement of particulate matter relative to the electrode; and correlating the measured current to a quantity of the particulate matter in the exhaust.

12. The method of claim 11, wherein the seed structure comprises dendric rhenium disposed on the surface of the electrode.

13. The method of claim 11, wherein the elongated members promote local charge concentration at tips of the elongated members to enhance a strength of a local electrical field.

14. The method of claim 11, wherein the elongated members promote an attraction of the particulate matter to tips of the elongated members.

15. The method of claim 11, wherein measuring the current further comprises measuring a change due to the charge transfer from the electrode to particles of the particulate matter via the seed structure.

16. The method of claim 11, wherein measuring the current further comprises measuring a change due to the charge transfer from the electrode to an agglomerate of the particulate matter via the seed structure.

* * * * *